United States Patent [19]

Ohmi

[11] Patent Number: 5,497,652
[45] Date of Patent: Mar. 12, 1996

[54] METHOD AND APPARATUS FOR EVALUATING QUANTITIES OF ABSORBED IMPURITIES

[76] Inventor: Tadahiro Ohmi, 1-17-301, Komegabukuro 2-chome, Aoba-ku Sendai-shi, Miyagi-ken 980, Japan

[21] Appl. No.: 142,466

[22] PCT Filed: May 13, 1992

[86] PCT No.: PCT/JP92/00604

§ 371 Date: Jan. 31, 1994

§ 102(e) Date: Jan. 31, 1994

[87] PCT Pub. No.: WO92/21956

PCT Pub. Date: Dec. 10, 1992

[30] Foreign Application Priority Data

May 30, 1991 [JP] Japan .................................. 3-155879

[51] Int. Cl.$^6$ .............................. G01N 31/06; G01D 18/00
[52] U.S. Cl. ...................... 73/31.03; 73/1 G; 73/23.21; 73/864.81; 436/8; 436/18
[58] Field of Search ..................... 73/31.03, 1 G, 73/23.21, 31.02, 864.81, 864.85, 23.2; 436/8, 9, 11, 18

[56] References Cited

U.S. PATENT DOCUMENTS

| | | | |
|---|---|---|---|
| 3,796,657 | 3/1974 | Pretorius et al. | 73/23.39 |
| 4,226,112 | 10/1980 | Jibelian | 73/23.1 |
| 4,302,422 | 11/1981 | Takahashi | 422/88 |
| 4,384,471 | 5/1983 | Wentzel | 73/23.1 |
| 4,668,091 | 5/1987 | Lagesson et al. | 356/246 |
| 5,214,952 | 6/1993 | Leggett et al. | 73/31.03 X |
| 5,221,517 | 6/1993 | Takeda | 422/54 |
| 5,305,630 | 4/1994 | Molozay et al. | 73/31.03 X |
| 5,325,705 | 7/1994 | Tom | 73/31.03 |

FOREIGN PATENT DOCUMENTS

| | | |
|---|---|---|
| 59-162403 | 9/1984 | Japan . |
| 61-79130 | 4/1986 | Japan . |
| 61-102538 | 5/1986 | Japan . |

*Primary Examiner*—Hezron E. Williams
*Assistant Examiner*—J. David Wiggins
*Attorney, Agent, or Firm*—Young & Thompson

[57] ABSTRACT

A method and device for evaluating the quantities of adsorbed impurities in sample gas of ultra-high purity for various kinds of materials. After inert gas of ultra-high purity is supplied to a sample-gas pipe(16) through a purifier(1)(a first gas-supply source), the inside of said sample-gas pipe(16) is baked by heater(19 to 20)(heating means). The inside of sample-gas pipe(16) is kept in an atmosphere at specified temperature and then changeover valves(9, 10) are changed over from opening to closing or vice versa so that the sample gas of a specified concentration is supplied from a bomb(6)(a second gas-supply source)into the sample-gas pipe(16) until the quantities of adsorbed impurities reach saturation, in other words, from the time when, sample gas flows into the pipe to that when a microanalyzer(25) detects said gas of said specified concentration.

12 Claims, 2 Drawing Sheets

METHOD AND APPARATUS FOR EVALUATING QUANTITIES OF ABSORBED IMPURITIES

TECHNICAL FIELD

The present invention relates to an evaluation method and device for determining quantities of absorbed impurities in common gases (argon gas, and the like) for use in, for example, semiconductor production, with respect to various types of materials.

BACKGROUND ART

In recent years, advances in semiconductor manufacturing technology have been striking, and there have been great demands for hyperfine structures; as a result of this, it has become necessary to maintain the environment of the manufacturing apparatus in a state of ultrahigh purity (that is to say, purity on the level of "ppt", or parts per trillion). As a result, in cases in which common gases of ultrahigh purity (for example, argon gas) are to be supplied through the medium of pipes which serve as gas flow conduits, it is necessary to determine, on the level of parts per trillion, the amount of impurities contained in the gas, such as moisture or the like, which adhere to the inner pipe surfaces, which comprise various materials.

Examples of conventionally known methods for the detection of adsorbed amounts include, for example, a method in which a microanalyzer (an atmospheric pressure ionization mass spectrometer) is connected to the pipe end of piping which is to be tested, a gas of ultrahigh purity is caused to flow into the piping from a gas purifier, and the amounts of impurities in the gas flowing out of the pipe end is measured.

However, in this conventional method, no account was taken of moisture which adhered to metal surfaces, and only the purity of the gas passing through the piping system which served as the gas conduit was measured, so that no precise determinations could be made with respect to the quality of the interior surfaces of the gas system.

The present invention was created in light of the above-described problems in the conventional technology; it has as an object thereof to provide an evaluation method and an evaluation device for quantities of absorbed impurities which are capable of evaluating, on the order of parts per trillion, quantities of impurities contained in a gas which adsorb to a gas conduit comprising various materials.

DISCLOSURE OF THE INVENTION

In order to attain the above object, the present invention contemplates a method wherein in a first step an inert gas of ultrahigh purity is caused to flow into a sample-gas pipe; in a second step, the interior of this sample-gas pipe is baked to reach at least the level of background purity; in a third step, the interior of this sample gas pipe is placed in an atmosphere having a specified temperature; in a fourth step, the inflow of a sample gas having a specified concentration into the sample gas pipe is initiated; and in a fifth step when the quantities of impurities within the sample gas which adsorb to the inner surface of the sample gas pipe reach saturation, the inflow of the sample gas is changed to the inflow of an inert gas.

In this case, it is preferable for the evaluation of adsorbed impurities that the sample gas pipe be freely replaceable with pipes comprising various materials, or the inner surfaces of which have been subjected to various types of processing.

Furthermore, it is preferable that the inert gas and sample gas comprise argon gas.

In order to carry out the method of the present invention, it is preferable that the inventive apparatus be provided with: a first gas supply source, for supplying an inert gas of ultrahigh purity, a second gas supply source, for supplying a sample gas, the added impurity amounts of which are freely adjustable, through the medium of a gas flow control meter; change-over valves, which are capable of freely selected change-over in order to cause either an inert gas or a sample gas to flow into the sample gas pipe, and which are connected to one end opening of the sample gas pipe; a support mechanism, for supporting the sample gas pipe; a microanalyzer, which is connected to the other end opening of the sample gas pipe; and a heating mechanism, which is capable of maintaining the interior of the sample gas pipe at a freely selected specified temperature.

In this case, it is preferable that the inert gas and the sample gas be passed through parts in contact with gas, the discharge gases of which are regulated so as to at least not worsen the highest purity level of each gas.

Furthermore, it is preferable that the microanalyzer comprise an atmospheric ionization mass spectrometer.

FUNCTION

First, by causing a gas of ultrahigh purity (that is to say, argon gas, or the like, having a purity of parts per trillion) to flow within a sample gas pipe which is to be the subject of evaluation, the interior of this sample gas pipe is placed in an atmosphere having a specified high level of purity. Next, a heating mechanism is brought into operation, and the interior of the sample gas pipe is baked at a specified high temperature so as to bring the atmosphere therein to at least a background level of purity. By means of this, the impurities which adhere to the inner walls of the sample gas pipe are caused to desorb. Next, the heating mechanism is controlled so as to bring the atmosphere within the sample gas pipe to a specified temperature. After this, a sample gas having a specified impurity concentration level is caused to flow into the sample gas pipe at a specified flow rate, and this gas is caused to flow into the sample gas pipe until the adsorbed impurities reach saturation. When saturation has been reached, the inflow of the sample gas is halted, baking is conducted by means of the heating mechanism so as to bring the interior of the sample gas pipe to an ultrahigh purity level, and the impurities which desorb from the sample gas pipe are detected.

Description of the References 1 gas purifier (first gas supply source)

6 bomb (second gas supply source)

9, 10, 11 first, second, and third valves (change-over valves)

15, 17 first and second joints (support mechanisms)

16 sample-gas pipe

25 APIMS (microanalyzer)
19, 20, 21 heaters (heating mechanisms)

BEST MODE FOR CARRYING OUT THE INVENTION

Figure 1:
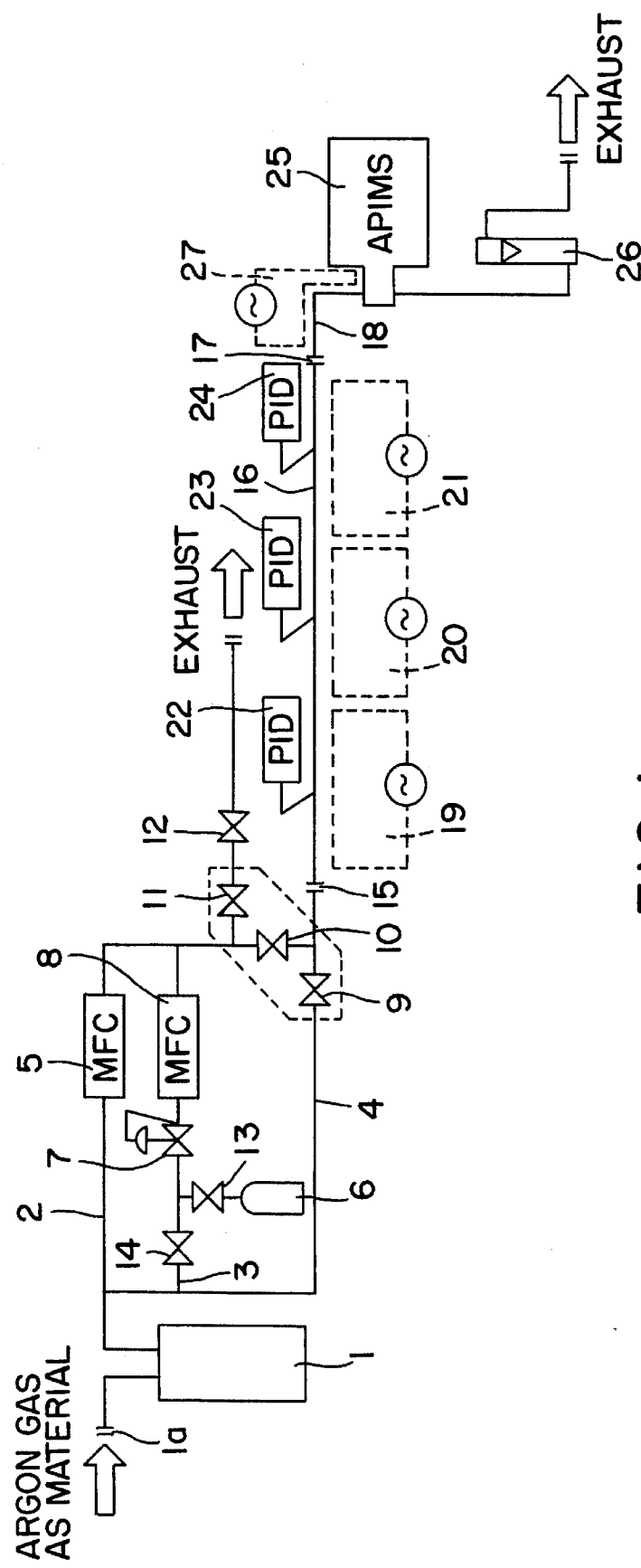
FIG. 1 is a gas flow diagram showing an example of a device for executing the evaluation method in accordance with the present invention.

FIG. 1 shows an example of a device for executing the evaluation method in accordance with the present invention. As shown in the figure, a supply source (not depicted in the figure) for a source gas which is an inert gas such as argon or the like, is connected to the gas inflow side of purifier 1 through the medium of gas joint 1a, and first through third gas supply lines 2–4 are connected to the gas blow-off side thereof.

A first gas flow control meter (MFC) 5 is connected to the first gas supply line 2, and bomb 6, regulator 7, and a second MFC 8 are connected to the second gas supply line 3 in that order from the upstream side as a supply source for moisture, which constitutes an impurity. Furthermore, a first valve 9 is connected to the third gas supply line 4, a second valve 10 and a third valve 11 are connected to the downstream side of the first and second MFCs 5 and 8, and a fourth valve 12 is connected to the downstream side of third valve 11.

A fifth valve 13 is provided on bomb 6, and this fifth valve 13 is connected to the upstream side of regulator 7, and is connected on the upstream side of regulator 7 along second gas supply line 3.

Here, by providing purifier 6, argon gas of ultrahigh purity (wherein the moisture concentration is, for example, on the level of at least 300 ppt) is obtainable, and if bomb 6 is filled with, for example, argon gas having a moisture concentration of 20–200 ppm, then, by means of the adjustment of regulator 7, argon gas having a freely selected moisture concentration (for example, 300 ppt-1500 ppb) is obtainable at the conflux portion of the first gas supply line 2 and the second gas supply line 3.

The first, second, and third valves, 9, 10, and 11 form an integrated change-over valve; the opening and closing of the first and third valves 9 and 11, and the second valve 10, is conducted exclusively. Furthermore, the first and second valves 9 and 10 are connected to one end of sample gas pipe 16 through the medium of a first joint 15, which comprises a support mechanism, and the other end of sample-gas pipe 16 is coupled with a transfer pipe 18 through the medium of a second joint 17, which forms another support mechanism. Furthermore, an appropriate number of heaters 19–21 are attached to the sample pipe 16 in the longitudinal direction thereof and are disposed by zone, and each heater 19–21 is capable of accurately controlling the temperature of the atmosphere of the sample gas pipe 16 within the corresponding zone. Furthermore, temperature detectors 22–24 for controlling the temperature are provided at each zone.

An atmospheric pressure ionization mass spectrometer (APIMS) 25 is connected to the transfer pipe 18 as a microanalyzer, and an exhaust mechanism is connected to the detection portion of APIMS 25 through the medium of a flow meter 26.

An exhaust mechanism is connected to a fourth valve 12, and a small heater 27 is attached to transfer pipe 18. Furthermore, the discharge gases of the portions in contact with gas, such as the valves 9, 10, and 11, and the gas joints, are regulated so as not to reduce the purity of the gases which pass therethrough.

Next, an evaluation method in accordance with the present example constructed in the above manner will be explained.

First, the sample-gas pipe 16, which is subject of the evaluation, comprises a stainless steel pipe, having, for example, a pipe diameter of ¼ inches (1 inch=2.45 cm) and a pipe length of 2 meters, and furthermore, the inner surface thereof has been subjected to electrolytic polishing, and furthermore, an oxide layer has been formed thereon, and this is placed between joints 15 and 17.

Next, the second valve 10 is closed, and the first valve 9 and the third-sixth valves 11–14 are opened, and the first and third gas supply lines 2 and 4, and sample-gas pipe 16 is purged by means of argon gas of ultrahigh purity. After this, heaters 19–21 are controlled so as to place the interior of sample-gas pipe 16 in an atmosphere having a high temperature, for example, 450° C.; that is to say, baking is conducted.

In this case, the first valve 9 is open, and the second valve 10 is closed, so that argon gas of ultrahigh purity (the moisture concentration thereof being, for example, of at least a level of 300 ppt) is caused to flow into sample-gas pipe 16 through the medium of first gas supply line 2.

Furthermore, at this time, the third and fourth valves 11 and 12, as well as the fifth and sixth valves 13 and 14 are opened, so that argon gas adjusted to a specified moisture concentration is blown off by means of an exhaust mechanism through the medium of second gas supply line 3 and third gas supply line 4. That is to say, argon gas having this moisture concentration can be supplied to sample-gas pipe 16 at a specified flow rate (for example, 1.2 liter/min). The adjustment necessary to provide the specified flow rate is conducted by means of first and second MFCs 5 and 8.

Baking is conducted until the interior of sample-gas pipe 16 reaches at least a background level of purity; the confirmation as to whether or not this level of purity has been reached is carried out by means of APIMS 25.

After it has been confirmed that the interior of sample-gas pipe 16 has reached a background level of purity, heaters 19–21 are controlled based on the output of temperature detectors 20–22 in order to cool the interior of sample-gas pipe 16 to a desired atmospheric temperature (for example, 23° C.). In this case, the small heater 27 is controlled so that transfer pipe 18 is also adjusted to a specified atmospheric temperature.

Next, from the above-described open and closed state of each valve, the second valve 10 is opened, and the first valve 9, as well as the third and fourth valves 11 and 12, are closed. By means of this, argon gas having a specified moisture concentration is caused to flow at a specified flow rate into sample-gas pipe 16 through the medium of second valve 10. By means of this inflow, moisture begins to adhere to the inner walls of sample gas pipe 16, so that the inflow initiation time is recorded.

The quantity of absorbed moisture is determined by the surface area of the inner wall of sample gas pipe 16, so that it reaches saturation at a predetermined amount. Accordingly, if the period of time from the initiation of the inflow of argon gas having the specified moisture concentration to the detection of argon gas having a specified moisture concentration by means of APIMS 25 is calculated, the saturation adsorption amount of the moisture can be evaluated.

When the quantities of adsorbed moisture reach saturation, from the above opened and closed states of the valves, the second valve 10 is closed, and the first valve 9, as well as the third and fourth valves 11 and 12, are opened. Then, heaters 19–21 are again controlled and baking is conducted so that the moisture adhering to the inner surface of sample-gas pipe 16 is desorbed.

Hereinafter, the above procedure is repeated in order to conduct measurement at other atmospheric temperatures (for example, 40° C., 60° C., 80° C., and the like).

Figure 2:
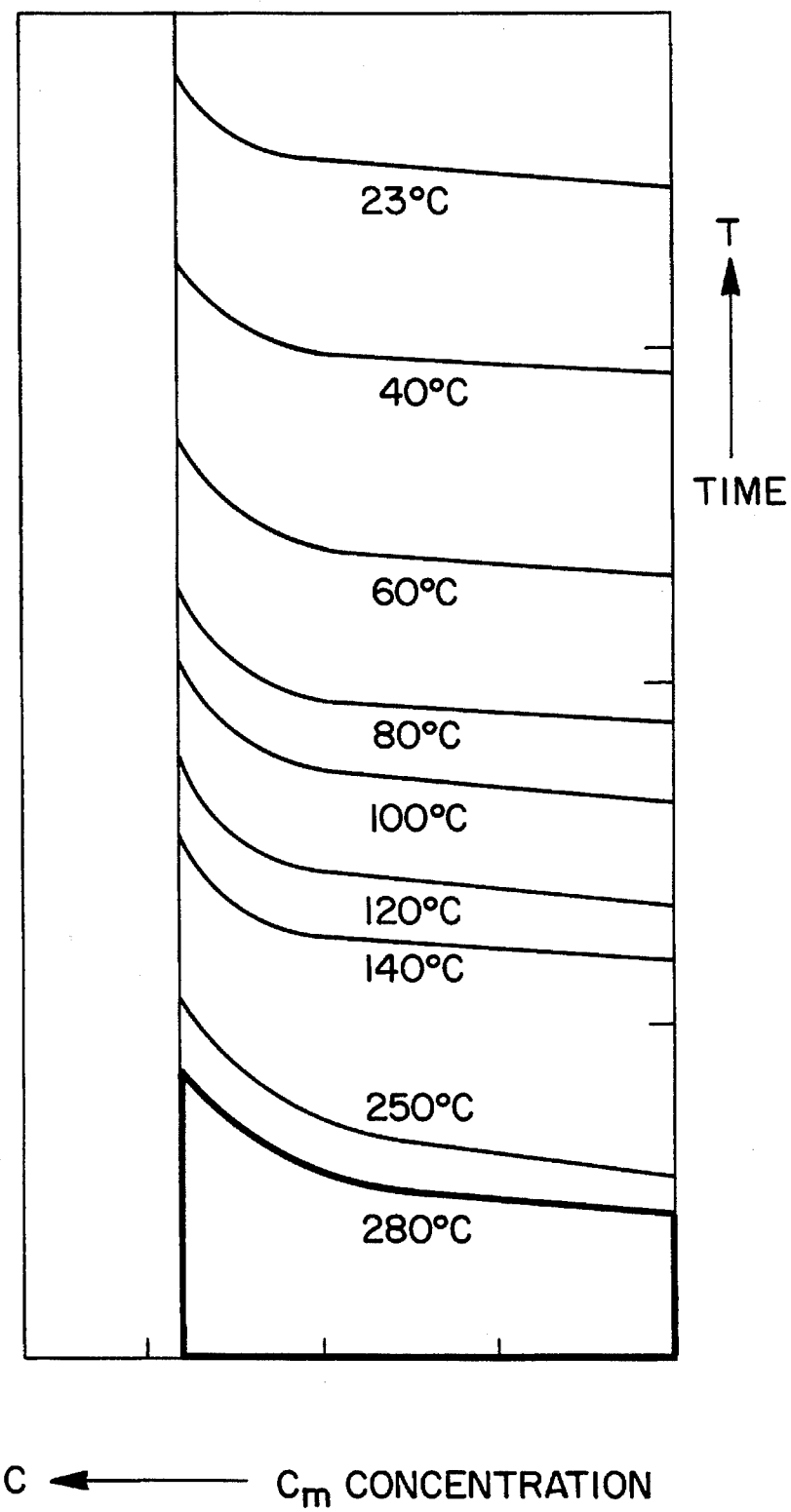
FIG. 2 is a graph showing the results of measurement by means of the device shown in FIG. 1.

FIG. 2 shows the results of the moisture adsorption evaluation of the sample gas pipe by means of the above method; the vertical axis indicates a time T, while the horizontal axis indicates a moisture concentration C within the sample gas (argon gas). That is to say, the point in time at which the moisture adsorption reaches saturation is approximately coincident with the point in time at which the concentration Cm of the argon gas which is caused to flow in is confirmed at the end of sample-gas pipe 16. Furthermore, it can be seen that as the atmospheric temperature within sample-gas pipe 16 increases, the time which elapses before adsorption saturation occurs becomes shorter.

By altering the materials or the inner surface processing method (film material or the like) of the sample-gas pipe 16, it is possible to conduct an evaluation of the moisture adsorption (the process is identical with respect to other impurities as well) with respect to various materials in an ultrahigh purity region.

INDUSTRIAL APPLICABILITY

In accordance with the invention, a first step, in which a inert gas of ultrahigh purity is caused to flow into a sample-gas pipe; a second step, in which the interior of the sample-gas pipe is baked so as to reach at least background purity level; a third step, in which the interior of the sample-gas pipe is set to a specified atmospheric temperature; a fourth step, in which the inflow of a sample gas having a specified concentration into the sample-gas pipe at a specified flow rate is initiated; and a fifth step, in which, when the quantity of impurities within the sample gas adsorbing to the inner surface of the sample-gas pipe reaches saturation, the inflow of the sample gas is switched to the inflow of an inert gas, are provided, so that it is possible to easily conduct the evaluation of impurity adsorption amounts at an ultrahigh purity level with respect to specified materials, and it is thus possible to contribute, in particular, to the manufacture of semiconductors having hyperfine structures.

Furthermore, in accordance with the invention, it is possible to easily conduct impurity evaluation with respect to various sample-gas pipes to be evaluated by means of the exchange of sample-gas pipes.

Furthermore, in accordance with the invention, it is possible to concomitantly use both a sample gas and a carrier gas for purging, and furthermore, measurement and handling is facilitated, as argon gas is physically and chemically stable.

What is claimed is:

1. A method for evaluating quantities of adsorbed impurities, the method comprising:
   a first step, in which an inert gas of ultra-high purity is caused to flow into a sample-gas pipe,
   a second step, in which an interior of said sample-gas pipe is baked to reach at least a level of background purity,
   a third step, in which said interior of said sample-gas pipe is placed in an atmosphere having a specified temperature,
   a fourth step, in which an inflow of a sample gas having a specified concentration into said sample-gas pipe is initiated, and
   a fifth step, in which, when quantities of impurities within said sample gas which adsorb to an inner surface of said sample-gas pipe reach saturation, said inflow of said sample gas is changed to an inflow of an inert gas.

2. A method for evaluating quantities of adsorbed impurities in accordance with claim 1, further comprising a step of exchanging said sample-gas pipe for sample-gas pipes made of various materials, and whose inner surfaces have been subjected to various types of processing.

3. A method for evaluating quantities of adsorbed impurities in accordance with claim 2, wherein the various materials for said sample-gas pipes are stainless steel, aluminum, or glass.

4. A method for evaluating quantities of adsorbed impurities in accordance with claim 2, wherein the inner surface of said sample-gas pipe has been subjected to electrolytic polishing, and has an oxide layer formed thereon.

5. A method for evaluating quantities of adsorbed impurities in accordance with claim 1, wherein said inert gas and said sample gas comprise argon gas.

6. A method for evaluating quantities of adsorbed impurities in accordance with claim 5, wherein said argon gas has a moisture concentration of 1500 ppb or below.

7. An apparatus for evaluating quantities of adsorbed impurities, the apparatus comprising:
   a sample gas pipe formed from materials which have a known affinity for adsorbing impurities from a sample gas flowing therethrough,
   a first gas supply source, for supplying an inert gas of ultrahigh purity,
   a second gas supply source, for supplying a sample gas, added impurity amounts of which are freely adjustable, through the medium of a gas flow control meter,
   change-over valves, which are capable of freely selected change-over in order to prevent either said inert gas or said sample gas from flowing into the sample-gas pipe, and which are connected to one end opening of said sample-gas pipe,
   support means for supporting said sample-gas pipe,
   a microanalyzer for analyzing gas impurities in a gas flow, said microanalyzer being connected to another end opening of said sample-gas pipe, and
   heating means for maintaining an interior of said sample-gas pipe at a freely selected specified temperature.

8. An apparatus for evaluating quantities of adsorbed impurities in accordance with claim 7, further comprising means for passing said inert gas and said sample gas through impurity adsorber parts in contact with gas, and means for regulating discharge gases to an extent such that a purity level of each said gas is at least not caused to decline.

9. An apparatus for evaluating quantities of adsorbed impurities in accordance with claim 8, wherein said parts in contact with gas are made of the same material as that of said sample-gas pipe.

10. An apparatus for evaluating quantities of adsorbed impurities in accordance with claim 7, wherein said microanalyzer includes an atmospheric pressure ionization mass spectrometer.

11. An apparatus for evaluating quantities of adsorbed impurities in accordance with claim 7, wherein said heating means include an appropriate number of heaters which are attached to said sample-gas pipe and spaced apart in a longitudinal direction thereof, and each of said heaters includes means for individually controlling the temperature.

12. An apparatus for evaluating quantities of adsorbed impurities in accordance with claim 7, wherein said sample-gas pipe and said microanalyzer are connected by a transfer pipe, and wherein said heating means include an appropriate number of heaters which are attached to said transfer pipe and spaced apart in a longitudinal direction thereof.

* * * * *